United States Patent [19]

Innerfield

[11] 3,985,618
[45] Oct. 12, 1976

[54] METHOD FOR DETECTION OF THROMBOSIS AND PRETHROMBOSIS

[76] Inventor: Irving Innerfield, 20 Knickerbocker Road, Tenafly, N.J. 07670

[22] Filed: Oct. 24, 1975

[21] Appl. No.: 625,628

Related U.S. Application Data

[63] Continuation-in-part of Ser. No. 574,181, May 2, 1975, abandoned.

[52] U.S. Cl. .................. 195/103.5 R; 23/230 B
[51] Int. Cl.² ........................................ C12K 1/04
[58] Field of Search ............. 195/103.5 R; 23/230 B

[56] References Cited
UNITED STATES PATENTS

| | | | |
|---|---|---|---|
| 2,878,715 | 3/1959 | Rhees | 195/103.5 R |
| 3,106,090 | 10/1963 | Barnes | 195/103.5 R |
| 3,853,710 | 12/1974 | Innerfield | 195/103.5 R |

*Primary Examiner*—A. Louis Monacell
*Assistant Examiner*—C. A. Fan
*Attorney, Agent, or Firm*—Blum, Moscovitz, Friedman & Kaplan

[57] ABSTRACT

The combination of two tests, a procoagulant assay (PA) and a heparin-procoagulant assay (H-PA) makes it possible to determine the status of a patient with respect to thrombosis and whether a prethrombotic condition exists. The results of the tests can be used to determine whether and what type of treatment is necessary.

9 Claims, 5 Drawing Figures

3,985,618

METHOD FOR DETECTION OF THROMBOSIS AND PRETHROMBOSIS

CROSS REFERENCE TO RELATED APPLICATION

This application is a Continuation-In-Part application of my co-pending application Ser. No. 574,181 filed May 2, 1975, and now abandoned for METHOD FOR DETECTION THROMBOSIS THROMOSIS AND PRETHROMBOSIS.

BACKGROUND OF THE INVENTION

The high incidence of coronary artery disease and the necessity for appropriate treatment, frequently on an emergency basis, lends great weight to the desirability for diagnostic tests which will rapidly establish the condition of a patient so that appropriate treatment may be prescribed. A second major group which needs close monitoring consists of women on the "pill". All of the oral contraceptives are based on estrogens, known to increase the tendency of the blood to clot. Some increase in the clotting tendency can be tolerated, but so far as those individuals who are more susceptible in this respect to the effects of the pill are concerned, it is necessary that this increased susceptibility be detected so that preventive measures can be taken.

A deviation in coagulability of the blood can be catastrophic in other types of patients such as those predisposed to thrombosis and thromboembolic disease. Similarly, it may be essential to detect a deviation from the clotting tendency norm in the direction of a decrease, since lack of adequate clotting factors may lead to bleeding, both internally and externally. In my U.S. Pat. No. 3,853,710 having the title "Serum Diagnostic Tests For Maladies Causing Change In Fibrinolytic Activity In The Blood," which issued on Dec. 10, 1974, there was disclosed a procoagulant (low FDP) assay. This assay, as will be shown, has also proved to be of significance with respect to the invention herein disclosed. Said patent is incorporated herein by reference as though fully presented.

SUMMARY OF THE INVENTION

In order to determine the status of a patient with respect to clotting of his blood, a sample is taken and subjected to two tests, the first of which is a procoagulant assay (PA) and the second of which is a heparin-procoagulant assay (H-PA). In the PA test, serum obtained from the blood of the patient is mixed with a standardized thrombin solution and then with a standardized plasma solution. The time of clotting is noted.

In the second of the tests, standardized plasma and thrombin solutions are prepared and to aliquots of serum taken from the patient's blood, different quantities of heparin are added. Each specimen of heparin-treated serum is individually mixed with thrombin and, after a period of incubation, with plasma. The clotting time is then noted. Also, similar tests are run on serum from healthy individuals. THe patients show four different test patterns so far as tendency to clot is concerned. As aforenoted, depending on the particular clotting pattern discovered by the results of the two types of tests, specific conditions requiring specific types of treatment are revealed.

Accordingly, an object of the present invention is to provide rapid and reliable means for determining the condition of an individual with respect to the tendency of the individual's blood to clot.

Another object of the present invention is to provide a rapid and reliable test for determining whether an individual is in need of emergency treatment with respect to an oncoming coronary artery event.

A further object of the present invention is a rapid and reliable method of determining whether the use of oral contraceptives may lead to clotting in a specific individual.

An important object of the present invention is a rapid and reliable test which will enable a physician to determine whether an individual requires either emergency or continued treatment with respect to a clotting abnormality.

A significant object of the present invention is a rapid and reliable test with respect to clotting of the blood where the test is amenable to automatic processing and/or diagnosis.

Yet another object of the present invention is a rapid and reliable test which can be used for routine screening of patients entering a hospital for virtually any reason to make certain that problems with respect to clotting of blood will not arise during treatment for seemingly non-connected conditions.

Still other objects and advantages of the invention will in part be obvious and will in part be apparent from the specification.

The invention accordingly comprises the several steps and the relation of one or more of such steps with respect to each of the others thereof, which will be exemplified in the method hereinafter disclosed, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
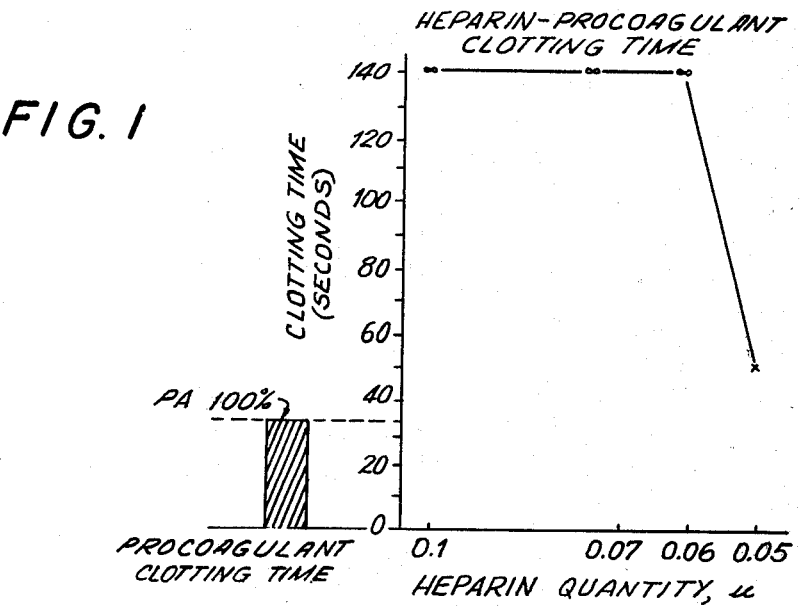
FIG. 1 is a graph of pattern A test results wherein PA and H-PA test results are both normal.

In preparation for running a test, a blood specimen is taken from a patient, allowed to stand for one half hour at room temperature to clot and the serum is then separated by centrifugation. Conveniently, centrifugation may be carried out at about 2000 rpm for about 15 minutes. The serum may be used immediately or may be stored at room temperature for a a period up to 6–8 hours. Usually two different tests, termed the PA and H-PA tests will be carried out on the serum.

Following are the procedures for the PA and H-PA tests:

STANDARDIZATION OF PLASMA AND THROMBIN FOR THE PA TEST

Normal plasma is prepared by dissolving 80 mg of solid plasma (TCC, available from Ortho Diagnostics) in 1 ml of distilled water. Thrombin solution is prepared by reconstituting thrombin (Fibrindex from Ortho Diagnostics, the package containing 50 units of thrombin) with 1 ml of saline solution. The thrombin solution is standardized by diluting with isotonic saline until 0.1 ml of the diluted thrombin clots 0.2 ml of normal plasma (both solutions equilibrated at 37°C) in 15 – 16 seconds. This thrombin solution is termed PA thrombin and is used only for the following PA test.

PROCOAGULANT ASSAY (PA TEST)

At least one but preferably several test tubes, each containing 0.2 ml of normal plasma are equilibrated in a 37°C bath. To 0.9 ml of standardized (PA) thrombin are added 0.1 ml of patient's serum in another test tube. The serum and thrombin are well mixed and the tube is placed in the 37°C bath to incubate for 3 minutes. At the end of the 3 minute incubation period, 0.1 ml of the thrombin-serum reaction mixture is removed and added rapidly to one of the plasma test tubes approximately simultaneously with removal of the plasma test tube from the bath. The addition is made under conditions such that the components are well mixed and a timer is started at the moment of addition of the thrombin-serum reaction mixture to the plasma. The time to the first appearance of a clot is noted as the PA time. Since there is a substantial change in the optical density of the mixture when the clot appears the formation and appearance of the clot can be detected either by eye or by the use of a suitable instrument incorporating a light beam, means for transmitting the light beam through the test tube and a detection system such as a photocell.

The extra tubes, each containing 0.2 ml of plasma, may be used for carrying out the test in duplicate or in triplicate as desired; alternatively, one or more of the extra tubes may be used for carrying out control tests or for tests on the blood of another patient.

The mean clotting time for serum of normal procoagulant activity, that is, for serum from healthy patients is 33 ± 2.5 seconds. A single standard deviation is then 11% of the clotting time. A clotting time below 30 seconds is considered low and a basis for action as will be indicated.

STANDARDIZATION OF PLASMA AND THROMBIN FOR THE H-PA TEST

Normal plasma is prepared by dissolving 80 mg of solid plasma (TCC, available from Ortho Diagnostics) in 1 ml of distilled water. Thrombin solution is prepared by reconstituting thrombin (Fibrindex from Ortho Diagnostics, the package containing 50 units of thrombin) with 1 ml of saline solution. The thrombin is standardized by diluting with isotonic saline until 0.1 ml of the diluted thrombin clots 0.2 ml of normal plasma in a test tube (both solutions equilibrated at 37°C) in 10.5–11 seconds, the clotting reaction by the tilt-tube method being initiated approximately simultaneously with removing the test tube containing the solution from the 37°C bath. Alternatively, if a conventional automatic thermostatting device is used, the tube containing the clotting reaction mixture is allowed to remain in the device at 37°C until the clotting endpoint. The clotting time is shortened by about one second by use of this latter technique; this change is considered negligible. This thrombin is termed H-PA thrombin and is used only for the following H-PA test.

HEPARIN-PROCOAGULANT ASSAY (H-PA)

Testing Procedure:

1. Pipette 0.2 ml of normal plasma into each of several glass test tubes and place in a water bath at 37°C to equilibrate.
2. Pipette 0.9 ml of standardized (H-PA) thrombin into each of several glass tubes. 3. Add 0.1 ml of serum from a patient to each of four test tubes, and to each test tube add 0.1 ml of one of four different heparin solution in normal saline, each 0.1 ml of heparin solution containing 0.1, 0.07, 0.06 and 0.05 heparin units respectively, mix the contents of each tube thoroughly. The heparin concentrations in the heparin-saline solutions will, of of course, be 0.1, 0.07, 0.06 and 0.05u/0.1 ml respectively or 1.0, 0.7, 0.6 and 0.5u/ml, where the symbol u indicates heparin units.
4. Add the heparin-treated serum from one of the four test tubes to a thrombin tube, mix thoroughly, place in the 37°C water bath, and start an interval timer.
5. After exactly 2 minutes of incubation, remove 0.1 ml of the thrombin-heparin-serum mixture, remove a plasma tube from the bath and approximately simultaneously add 0.1 ml of thrombin-heparin-serum mixture to the tube containing 0.2 ml of plasma under conditions such as to mix the contents thoroughly. Here also, if an automatic device is used, the clotting reaction can be carried out in the device at 37°C. Start a stop-clock simultaneously with adding the thrombin-heparin-serum mixture with the plasma and record the clotting time in seconds. Repeat the process using 0.1 ml of heparin-treated serum from each of the other three test tubes, recording the clotting time again. It is sufficient to keep the thrombin-heparin-serum mixture under observation for 180 seconds.

The mean normal control clotting time for serum from healthy patients is greater than 180 seconds when the 0.1 ml of serum is diluted with 0.1 ml aliquots of heparin solutions, the 0.1 aliquots containing respectively 0.1, 0.07 and 0.06 heparin units. For the serum diluted with a heparin solution containing 0.05 heparin units, the clotting time is 60 ± 12 seconds.

To evaluate the tests for serum coagulability disclosed herein, serum from three groups of patients were studied by means of PA and H-PA tests. Group 1 consisted of 25 healthy individuals (students, nurses, technicians). Group II consisted of 39 women who had been taking contraceptive pills for periods varying from 3 weeks to 5 years. In Group III were 8 patients hospitalized with recent acute thrombophlebitis, 4 patients with arterial emboli, 3 patients with atherosclerotic occlusive arterial disease and 7 patients with recent pulmonary emboli (proved by lung scan).

The test results were found to fall in four patterns as follows:

A. NORMAL PA; NORMAL H-PA

Each normal individual, and 4 of the 39 "pill" patients (10%) showed this pattern. (PA test clotting time at least 30 seconds).

B. PA NORMAL; H-PA INTERMEDIATE

The H-PA test result is considered intermediate if the serum specimen to which was added the heparin solution containing 0.1u clots in 40 – 180 seconds. As before, the PA test result is considered normal if the clotting time is at least equal to about 88% of normal which corresponds to 30 seconds.

Of 39 patients on the "pill" 29 (74%) showed this pattern. The 3 patients with arterial occlusion (non-embolic) were in this group.

The PA test indicated that fibrinogen degradation products, also termed FDP as well as split products, were not increased. The H-PA test results indicated that there was a slight increase in procoagulant in the serum in the individuals with clotting test results corresponding to pattern B. As is known, women on the pill have a slightly increased tendency to form clots, but where the H-PA clotting time is in the range specified, no action need be taken.

C. PA LOW; H-PA INTERMEDIATE

Of 39 patients on the "pill," four (10%) showed this pattern. Split products were increased in two of the four. One of the 4 patients with an arterial embolus was in this group and also had increased split products.

For a pattern C woman on the "pill," the dosage should be cut down either by reducing the quantity of estrogen or the frequency of use. Further, use may be made of clot-preventive therapeutic agents, i.e., aspirin and dipyridamole.

D. PA LOW; H-PA LOW

Of 39 patients on the "pill," two (6%) showed this pattern. The clotting time on the PA test is considered low when it is below about 30 seconds. The result on the H-PA test is considered low when the clotting time for the serum sample containing 0.1 $\mu$ of heparin is below 40 seconds.

In addition to the two patients on the "pill," the eight patients with acute thrombophlebitis, the 7 patients with pulmonary emboli and three of the four patients with arterial emboli showed this pattern.

Patients showing the D pattern require treatment on an emergency basis with appropriate therapeutic agents such as heparin, etc.

It should be noted that the assays presented herein are carried out on serum and not on plasma. Procoagulant activity as indicated by the PA results is about 35% more in serum than in plasma. This phenomenon has been ascribed to antithrombin "consumption" during clotting. However, no significant difference between serum and plasma with respect to Antithrombin-III (AT-III) content was found, the assay being carried out on serum and plasma specimens from healthy individuals by immunoelectrophoresis against a known antibody monospecific for human AT-III.

The PA test results mirror the algebraic sum total of antithrombins vs. procoagulants. The results presented above support the view that serum procoagulant activity is more than that of plasma because serum contains more platelet-derived procoagulants, particularly platelet factor 4. Furthermore, immunoassays for AT-III were normal in each of the three groups examined. These observations support the view that decreased PA clotting times in Group II and Group III patients were not due to decreased AT-III and strengthen the causative association with circulating procoagulants. It also validates the hypothesis that the haemostatic inbalance in patients having coronary artery disease and giving low PA test results is due to predominance of procoagulants over antithrombins.

Figure 2:
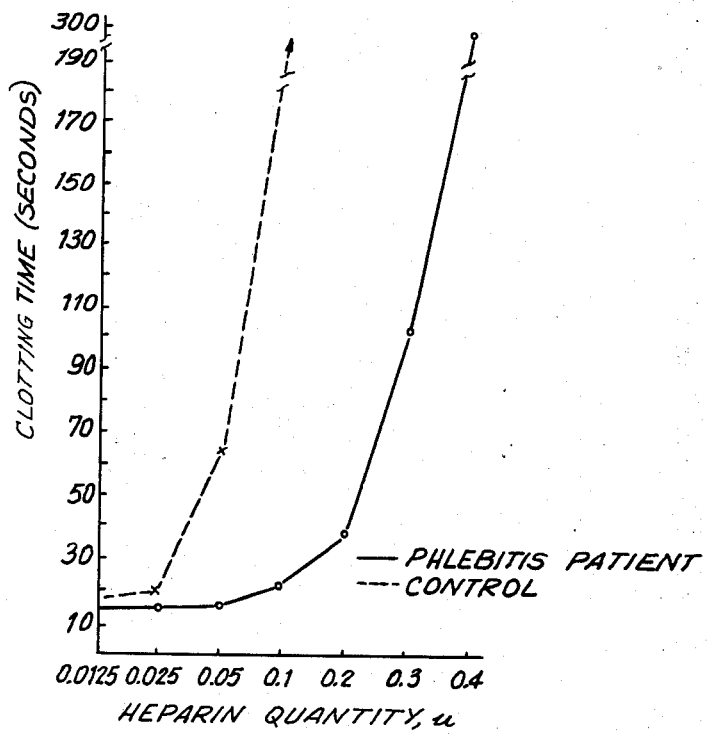
FIG. 2 is a graph showing the clotting time in acute thrombophlebitis compared with a normal control on the H-PA test.

AT-III is known to be heparin co-factor, and antithrombin activity is markedly enhanced when heparin combines with AT-III. As can be seen from FIG. 1 when heparin in quantities of 0.1, 0.07, 0.06 and 0.05$\mu$ was added to 0.1 ml of normal serum, clotting occurred only at the 0.05 $\mu$ level. In contrast, when the H-PA test was run on serum from a patient with acute thrombophlebitis, clotting occurred in only 22 seconds despite the addition of 0.1 ml of a solution containing 0.1 $\mu$; this finding is to be compared with infinity clotting time for the normal control, also shown in FIG. 2. In the thrombophlebitis patient, infinity clotting time was reached only after 0.4 $\mu$ was added, while for the control, also shown in FIG. 2, infinity clotting time was reached with only 0.1 $\mu$. It appears that when increasing concentrations of heparin were added to the serum of the thrombophlebitis patient, the H-PA test results remained constant, perhaps due to insufficient AT-III-heparin complex formation, until the amount of heparin exceeded the total anti-heparin factors in the serum. According to FIG. 2, the concentration of heparin needed to initiate an increase in clotting time was about 0.2 $\mu$ and 0.4 $\mu$ was needed for incoagulability. In contrast, normal serum is incoagulable even at 0.1 $\mu$ of heparin addition. Thus, the H-PA test seems to reflect total serum anti-heparin activity, i.e., total procoagulant, rather than any single anti-heparin component such as platelet factor 4, factor XIa, factor IXa, factor Xa or thrombin.

Figure 3:
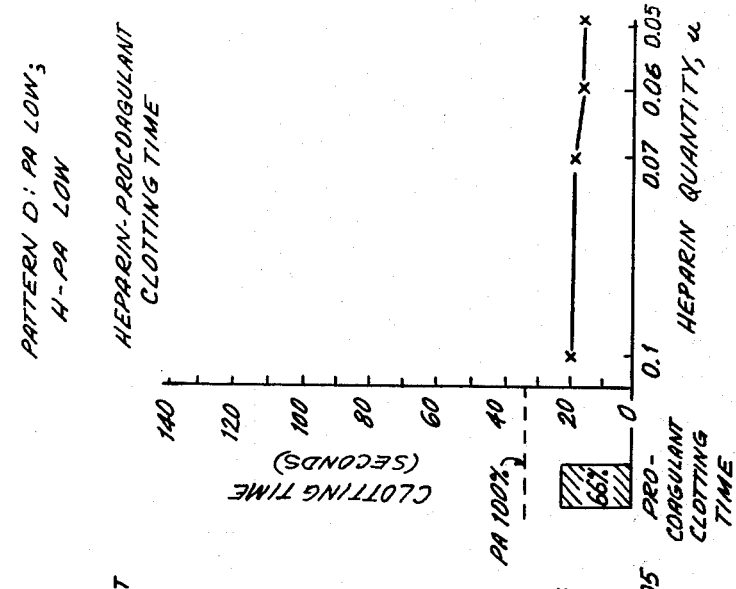
FIG. 3 is a graph of pattern B test results wherein the PA test results are normal and the H-PA test results are intermediate.

It therefore appears that the combination of PA and H-PA assays is useful in ascertaining whether the clotting system has become "triggered" or activated, as well as ascertaining the extent of such activation. When either test is used alone, this important delineation can be missed, as has been found in several instances. This is illustrated in patients with test patterns B and C. A majority of women on the "pill" (29 out of 39 or 74%) developed pattern B which consists of a normal PA and an intermediate H-PA. The results are shown in FIG. 3. This pattern represents the earliest and probably the mildest form of a "triggered" clotting system. It would have been missed if only the PA test had been carried out since the clotting time was 88% or, roughly, within one standard deviation of the mean clotting time. None of the 29 patients in this group showed increased FDP split products.

Parenthetically, it is noted that it is considered that a result on the PA test which differs from the mean by more then one standard deviation should alert the physician to the possibility of the presence of a pathological condition. Normally, the position is taken that a hypothesis is doubtful unless a test result differs from the mean by at least two standard deviations. Such a difference corresponds to a probability of 19 in 20 that the hypothesis is correct. However, it is suggested that in evaluation of results of the PA test a conservative position should be taken, namely, where the difference exceeds one standard deviation, further analysis of the situation is indicated. This position is consistent with the way in which the test results have been allocated to the various patterns.

Figure 4:
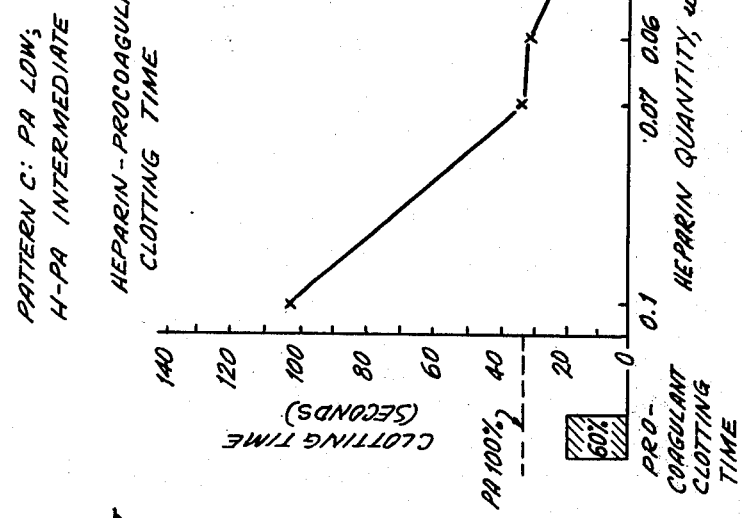
FIG. 4 shows graphically pattern C test results wherein the PA test results are low and the H-PA test results are decreasing.

The normal PA results in pattern B differentiate this pattern from pattern C in which the PA results are low but the H-PA results remain intermediate as shown in FIG. 4. This pattern is found in four "pill" patients, three with (non-embolic) arterial occlusive disease and one with arterial embolus, and represents a more extensively "triggered" clotting system, which again would have been missed without the accompanying PA data. The average clotting time on the PA test was 60% of normal, or 20 seconds. Split products were increased in two of the four "pill" patients and in the patient with arterial embolus. Three patients with atherosclerotic occlusive vascular disease exhibited pattern B. This would imply that intravascular fibrin deposition is essential for patterns C and D in peripheral vascular disease.

Figure 5:
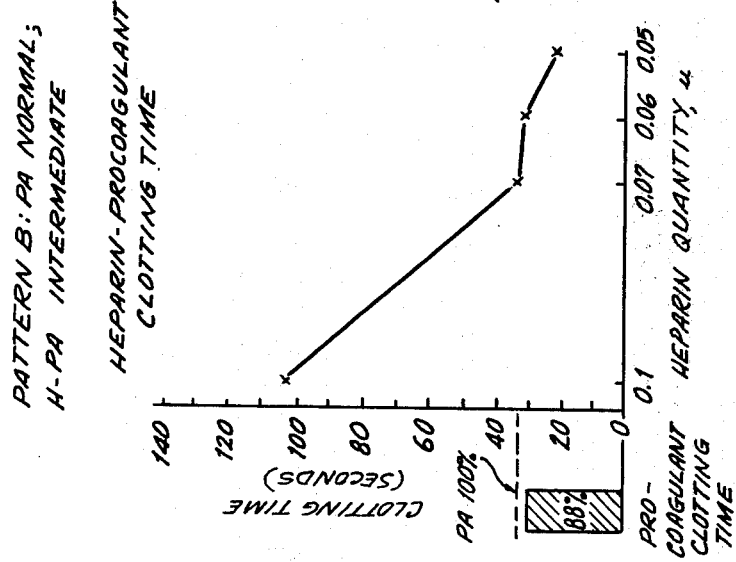
FIG. 5 is a graph of pattern D test results in which both the PA and H-PA test results are low.

It would appear that for patterns A and D, the H-PA test alone is sufficient. It is highly impressive that each patient with venous thrombosis or pulmonary embolus and three of the four patients with arterial emboli had strikingly low PA and H-PA results as shown in FIG. 5. It will be noted that the clotting time in the H-PA test was less than 20 seconds even when the quantity of heparin added in the test was 0.1 $\mu$. Consequently, the H-PA test alone, was enough to indicate a serious pathology. On this point of the H-PA test sufficing for patterns A and D, it should be noted that a normal H-PA test result is obtained only for pattern A. In short, a normal H-PA test is obtained only for pattern A and a low H-PA test is obtained only for pattern D.

It may useful to lable the test pattern C as indicating patients in a "pre-thrombotic" range and pattern B as indicating patients in "pre-pre-thrombotic" range. The high incidence of women on the "pill" who show patterns B and C may make contraceptive medication less empirical and further reduce the already slight incidence of thromboembolism associated with contraceptives by adjusting dosage to a specific level of PA and H-PA activity. This can be done by decreasing the quantity of estrogen taken with each dose or by decreasing the frequency of dosage. Most significantly, the PA and H-PA assays make it possible to identify thrombosis-prone and thrombotic individuals in whom antiplatelet or anticoagulant therapy might be beneficial. Such therapy can be carried out by administering drugs such as aspirin and dipyridamole.

It is recognized that many variations of the procedures described herein are possible for achieving the same results. Thus, the concentration at which the thrombin is used could be varied, the temperature and time of incubation in the PA test procedure could be changed and different heparin concentrations and reaction temperatures could be used in the H-PA test. However, it would be well within the ability of one skilled in the art to make such changes and then to establish appropriate values for clotting times on both the PA and the H-PA tests to delineate results into the four patterns described herein. Moreover, it is recognized that when the results on the H-PA test are either normal or low, that is, not intermediate, it is unnecessary to run the PA test. Nevertheless results obtained on the PA test may serve as useful confirmation that the patient is in pattern A or D.

It will thus be seen that the objects set forth above, among those made apparent from the preceding description, are efficiently attained and, since certain changes may be made in carrying out the above method without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method of measuring serum coagulability in a patient comprising the steps of adding heparin in different amounts to aliquots of serum from a patient, adding each of the resultant heparin-serum solutions to a separate tube containing thrombin solution, reacting a portion of each of the resultant thrombin-heparin-serum solutions with normal plasma solution to determine whether clotting occurs, and in the event clotting occurs, determining the clotting time, all steps being carried out under standardized conditions at at least one selected temperature, thereby making it possible to compare the measured clotting times with clotting time ranges obtained under standardized conditions with serum from healthy unmedicated individuals and from known thrombotic individuals, and to establish whether the measured clotting times fall within a first normal range corresponding to normal, unmedicated individuals, a second low range corresponding to thrombotic individuals, or third and fourth ranges intermediate said normal and low ranges and corresponding to individuals of increasing coagulability, a low clotting time correlating with high serum coagulability.

2. The method of measuring serum coagulability in a patient as defined in claim 1, further comprising the steps of reconstituting solid plasma with distilled water to prepare normal plasma, reconstituting solid thrombin with isotonic saline to form a thrombin solution, and standardizing said thrombin solution by diluting same with isotonic saline until 0.1 ml of diluted thrombin solution clots 0.2 ml of normal plasma in 10.5 – 11 seconds, both the thrombin and the plasma solutions being at 37°C.

3. The method of measuring serum coagulability in a patient as defined in claim 2 wherein said aliquots are four in number and are each 0.1 ml in volume, the quantities of heparin added to said four aliquots being 0.1 ml of solution containing respectively, 1.0, 0.7, 0.6 and 0.5 heparin units.

4. The method of measuring serum coagulability in a patient as defined in claim 3, further comprising the steps of adding each of said heparin-serum solutions to 0.9 ml of standardized thrombin solution, incubating said heparin-serum-thrombin solutions at 37°C for 2 minutes, adding 0.1 ml of each of said incubated solutions to a separate tube each containing 0.2 ml of normal plasma equilibrated at 37°C, and noting the clotting times for the contents of each of said tubes.

5. The method of measuring serum coagulability in a patient as defined in claim 1, wherein said clotting times are noted by an automatic device.

6. The method of measuring serum coagulability in a patient as defined in claim 1, further comprising the steps of mixing a further portion of serum from a patient with a quantity of a second thrombin solution, mixing a portion of said thrombin-serum mixture with a further portion of plasma, all steps being carried out under standardized conditions, and noting the clotting time, thereby making it possible to compare the measured clotting time of said mixed portion of second thrombin solution, serum and plasma with the clotting time range obtained under standardized conditions with serum from healthy, unmedicated individuals and with serum from patients suffering from known pathologies, a clotting time below the range characteristic of healthy, unmedicated individuals indicating a decrease in fibrinogen degradation products.

7. The method of measuring serum coagulability in a patient as defined in claim 6, further, comprising the steps of reconstituting solid plasma with distilled water to form normal plasma, reconstituting solid thrombin with isotonic saline to form a second thrombin solution, and standardizing said second thrombin solution by diluting same with isotonic saline until 0.1 ml of diluted second thrombin solution clots 0.2 ml of normal plasma in 15 – 16 seconds.

8. The method of measuring serum coagulability in a patient as defined in claim 7, wherein said quantity of second thrombin solution is 0.9 ml, said further portion of serum is 0.1 ml, said further portion of plasma is 0.2 ml, said further portion of plasma having been equilibrated at 37°C, the quantity of thrombin-serum mixture mixed with said further portion of plasma being 0.1 ml and further comprising the steps of incubating said mixture of said second thrombin solution and said further portion of serum at 37°C for 3 minutes immediately prior to adding 0.1 ml thereof to said further portion of plasma, and observing the clotting time of the plasma-thrombin-serum mixture.

9. The method of measuring serum coagulability in a patient as defined in claim 8, wherein the clotting times of said mixed second thrombin solution and further portions of serum and plasma are noted by an automatic device.

* * * * *